United States Patent [19]

Tsunoyama et al.

[11] Patent Number: 4,690,558

[45] Date of Patent: Sep. 1, 1987

[54] METHOD OF LASER EMISSION SPECTROSCOPICAL ANALYSIS AND APPARATUS THEREFOR

[75] Inventors: Kouzou Tsunoyama, Chiba; Yoshiharu Ohashi, Setagaya; Yasuko Furunushi; Motoyuki Konishi, both of Chiba, all of Japan

[73] Assignee: Kawasaki Steel Corporation, Japan

[21] Appl. No.: 682,835

[22] Filed: Dec. 18, 1984

[51] Int. Cl.$^4$ ............................................. G01N 21/63
[52] U.S. Cl. ................................................... 356/318
[58] Field of Search ............... 356/317, 318, 417, 313, 356/306

[56] References Cited

U.S. PATENT DOCUMENTS 3,102,921  9/1963  Peras ............................... 356/306 X
3,791,743  2/1974  Cody et al. ........................ 356/417
4,255,051  3/1981  Imamura et al. ..................... 356/306

OTHER PUBLICATIONS

Jannitti et al, "Observations of Light Back-Scattered From a Laser Produced Plasma", *Optics Communications*, vol. 10 #2, Feb. 1974, pp. 186-190.

Marich et al, "Improved Q-Switched Ruby Laser Microprobe For Emission Spectroscopic Element Analysis", *Journal of Physics E*, Oct. 1974, pp. 830-834.

*Primary Examiner*—Vincent P. McGraw
*Attorney, Agent, or Firm*—Parkhurst & Oliff

[57] ABSTRACT

In a method of laser emission spectroscopical analysis, wherein a light emitted from the surface of a sample when a laser beam is irradiated onto the surface of the sample is spectroscopically analyzed, an emission mode of the laser beam is fixed to a gauss distribution type $TEM_{00}$ mode to avoid variations in an intensity distribution due to a change in mode, and an analyzed value is obtained from an intensity of a spectral line of an element to be measured when an intensity of a preset spectral line or an intensity ratio between a pair of preset spectral lines is within a predetermined range, so that the influence of wide fluctuations in an evaporation and an excitation processes occurring on the surface of the sample can be eliminated, thereby improving the accuracy of analysis.

6 Claims, 3 Drawing Figures

METHOD OF LASER EMISSION SPECTROSCOPICAL ANALYSIS AND APPARATUS THEREFOR

BACKGROUND OF THE INVENTION

1. Field of the Invention

This invention relates to a method of laser emission spectroscopical analysis and an apparatus therefor, and more particularly to improvements in a method of laser emission spectroscopical analysis and an apparatus therefor, wherein a light emitted from the surface of a sample when a laser beam irradiates the surface of the sample is spectroscopically analyzed, and which are suitable for use in direct analysis of hot metal, molten steel, slag and the like.

2. Description of the Prior Art

With the progress of the laser technique, in various fields, there have been attempts to use lasers as a source of excitation to conduct an emission spectroscopical analysis. More specifically, when a powerful laser beam adapted to be focused on the surface of a sample by a focusing lens having a suitable focal length irradiates the surface of the sample, a surface layer of the sample is rapidly heated. Particularly, if the laser beam is formed into pulse shapes of several ten nanosecond, then such conditions occur that energy is locally poured into the sample before heat is diffused in the sample, whereby melting and evaporation occur. Vapor is further excited by the laser beam to be formed into plasma which emitts a light. According to the method of laser emission spectroscopical analysis, this light is transmitted to a spectroscope by means of a suitable light introducing system, spectrally separated by a diffraction grating and the like and formed into spectra, and thereafter, detected by a photographic film, a photomultiplier tube, a photo-diode and the like, whereby contents of aimed elements are determined. This method has such outstanding characteristic features that the method is also applicable to non-electrically conductive materials, can make analysis in atmosphere and so on. However, the method has disadvantages insofar as variations in data are high and the accuracy of analysis is unsatisfactory. The major cause is generally considered to reside in the variations in the output intensity of the laser, with the result that such a method has been normally adopted that the intensity of laser is constantly monitored by a suitable method and data are normally collected only within a predetermined range. However, this method has been disadvantageous in that it is impossible to cope with changes in the distribution of the intensities of laser beams and the adverse influence of the variations in the evaporation and excitation processes due to the contour of the surface of the sample and also due to the presence of contaminations, an oxide layer and the like cannot be removed.

SUMMARY OF THE INVENTION

The present invention has been developed to obviate the above-described disadvantages of the prior art and has as its object the provision of a method of laser emission spectroscopical analysis and an apparatus therefor, wherein an analysis can be conducted with high accuracy irrespective of variations in the output intensity of laser and the like.

To this end, the present invention contemplates that, in the laser emission spectroscopical analysis, wherein, a light emitted from the surface of a sample when a laser beam irradiates the surface of the sample, is spectroscopically analyzed, the emission mode of the laser beam is fixed to a gauss distribution type $TEM_{00}$ mode and an analyzed value is obtained from an intensity of a spectral line of an element to be measured when the intensity of a preset spectral line or the intensity ratio between a pair of preset spectral lines in the light emitted from the sample is within a preset range.

The present invention has been achieved on the basis of the results of the present inventors study of the variations in intensity of spectral lines, which variations are regarded as a drawback in the laser emission spectroscopical analysis. During the course of their study, the present inventors found the following:

(1) If an output from a laser oscillator is increased, then the coefficient of variation (one obtained by dividing a standard deviation by a mean value) of the intensity of a spectral line decreases. However, if an amplifier is positioned in a stage posterior to the laser oscillator and the output is further increased, then the coefficient of variation of the intensity of the spectral line increases, to the contrary.

(2) When the amplifier is not used and a laser beam is obtained only by a laser oscillator, the variation of the intensity of spectral line is higher than the variation of the output of laser.

FIGS. 1 and 2 show the results of experiments. The sample used in the experiments was an Fe alloy. An infrared laser having a wavelength of 1.06 micrometer and a pulse width of 15 nanosecond was used to provide the laser beam. As apparent from FIG. 1, when the output of laser exceeds an output of 2 joule obtained through the utilization of an amplifier, the coefficient of variation suddenly increases. The cause is believed to reside in the intensity distribution of laser pulses. More specifically, in the intensity distribution (mode) of a laser beam emitted from a laser oscillator in the direction of vertical section, there are generally various symmetries. When such a high output such as is used in the emission spectroscopical analysis is required, there is adopted a multi-mode oscillation in which modes are changed over from one to another per pulse. However, if an amplifier is actuated when peaks of several intensity distributions are present in a beam as described above, then a specified peak becomes amplified preferentially. Consequently if a laser beam having the above-described intensity distributions is converged onto the surface of a sample, then, in the spot caliber thereon, a zone of a high irradiation density occurrs locally. Since such wide fluctuations in the irradiation density are varied from a pulse to another, the intensities of emission spectra are varied. Then, the present inventors thought of also fixing the laser beam used in the emission spectroscopical analysis to the $TEM_{00}$ mode in which the guass distribution type output is obtainable through the utilization of a mode lock method used in the holography and the like. Although $TEM_{01}$ mode and the like in which an annular distribution is obtainable may be utilized as such a mode described above, it is believed that the guass distribution is most suitable for the emission spectroscopical analysis. Additionally, if the mode lock is adopted, the laser output decreases. However, an output of the laser oscillator is increased and another amplifier is added for use, so that this decrease in the laser output can be made up for. Needless to say, when the laser beam is fixed to $TEM_{00}$ mode, even if the amplifier is utilized, the mode is not changed.

On the other hand, FIG. 2 shows a comparison between the coefficient of variation (solid line A) of 271.4 nanometer wavelength Fe spectral line intensity and the coefficient of variation (solid line B) of the laser output when a laser beam identical with that shown in FIG. 1 irradiates an Fe alloy. In spite of non-use of the amplifier, the variations in intensity of spectral line are larger than the width of variation of the laser output. The above-described variation in intensity of emission spectra can be improved by the aforementioned mode lock. In addition to this, the influences of wide fluctuations in an evaporation and an excitation processes occurring on the surface of the sample during the irradiation of laser cannot be disregarded. Since the latter cannot be removed solely by controlling the laser output and the mode, it has been thought in the past when a predetermined spectral line such as an Fe alloy which is obtainable during the irradiation of laser is used, one or two of Fe spectral lines each having a suitable wavelength have been selected, the intensity or the intensity ratio thereof is constantly monitored, and the spectral line intensity of an aimed element to be measured is read only within the preset variation range. Particularly, the latter method of regulating the intensity ratio can restrict the temperature of the plasma produced by the irradiation of laser, thus being effective in improving the accuracy of analysis.

The present invention has been attained on the basis of the above-described knowledge.

According to the present invention, an analysis with high accuracy can be conducted irrespective of the variations in the laser output intensity and the like.

While 13.0% was obtained when the coefficient of variation of the spectral line intensity measured according to the conventional method in measuring Si spectral line intensity of 288.2 nanometer wavelength in an Fe alloy, the coefficient of variation was improved to 9.0% when the laser output was fixed to $TEM_{00}$ mode. Further, according to the present invention, the laser output was fixed to $TEM_{00}$ mode, and only when the 271.4 nanometer wavelength Fe spectral line intensity being monitored was within the range of plus-minus 5% of a predetermined value, 288.2 nanometer wavelength Si spectral line intensity was read, then 7.3% was obtained. Furthermore, also, according to the present invention, the laser output was fixed to $TEM_{00}$ mode, two Fe spectral lines of 271.4 nanometer wavelength and 273.1 nanometer wavelength were monitored, and Si spectral line intensity was read when the intensity ratio thereof was within the range of plus-minus 5% of a predetermined value, then 5.9% was obtained. It was ascertained that, in the cases of the both methods as described above, the coefficient of variation in the spectral line intensity became small as compared with the case of the conventional method or the case of only fixing the laser output to $TEM_{00}$ mode.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

Detailed description will hereunder be given of one embodiment of the apparatus of laser emission spectroscopical analysis, in which is adopted the method of laser emission spectroscopical analysis according to the present invention with reference to the drawings.

Figure 1:
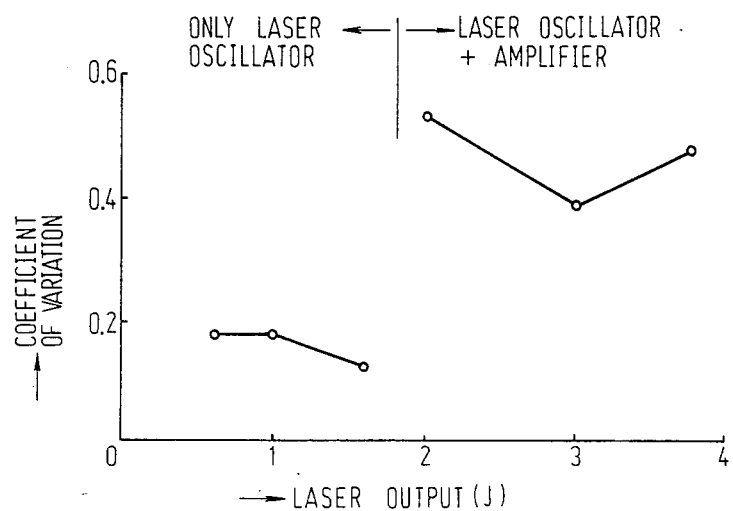
FIG. 1 is a chart showing the relationship between the laser output and 271.4 nanometer wavelength Fe spectral line intensity.
Figure 2:
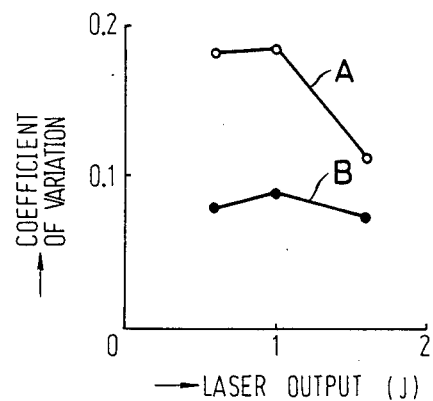
FIG. 2 is a chart showing a comparison between the laser output, the coefficient of variation of the laser output and the coefficient of variation of 271.4 nanometer wavelength Fe spectral line intensity.
Figure 3:
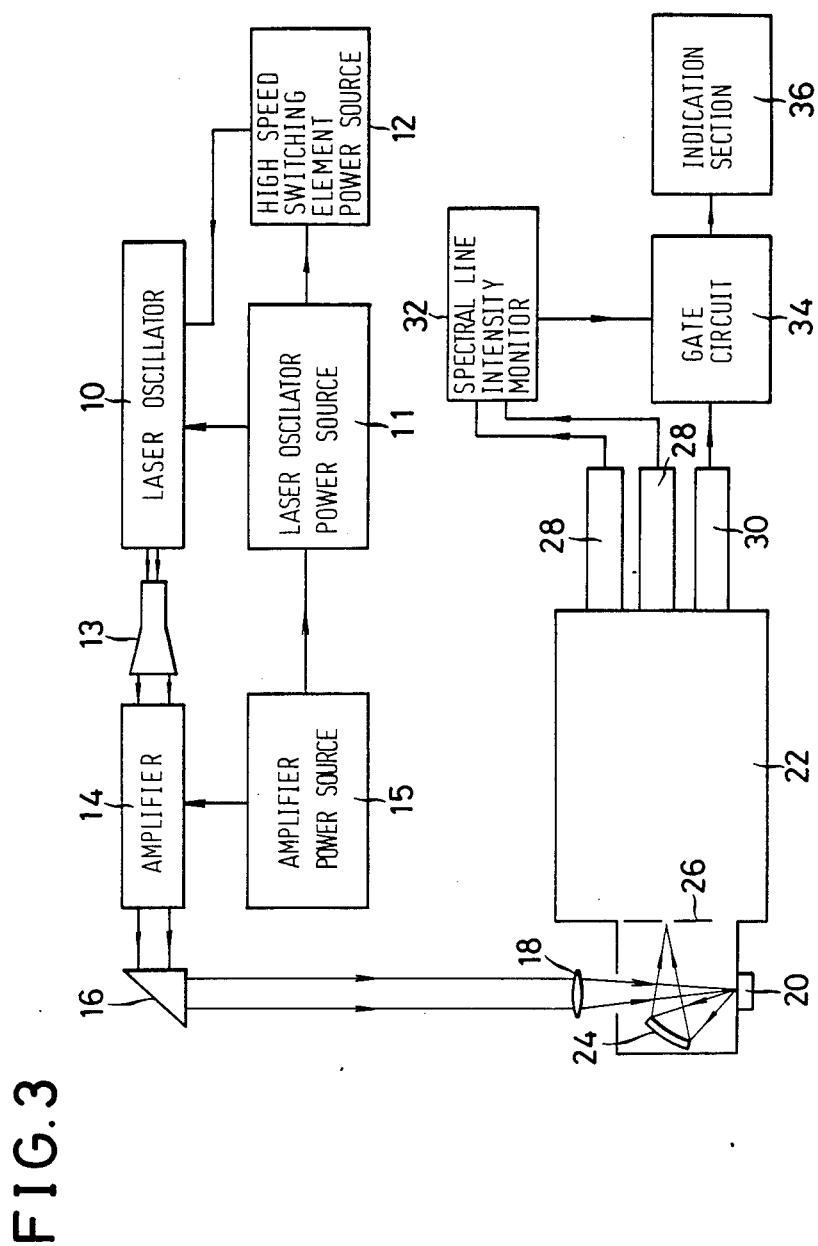
FIG. 3 is a block diagram showing the arrangement of one embodiment of the laser emission spectroscopical analysis, in which is adopted the method of laser emission spectroscopical analysis according to the present invention.

As shown in FIG. 3, this embodiment comprises:

a laser oscillator 10 assembled thereinto with a mechanism for the mode lock, not shown, for oscillating a laser beam;

an oscillator power source 11 for driving the laser oscillator 10;

a power source 12 of a high speed switching element, for actuating a high speed switching element, not shown, assembled into the laser oscillator 10;

an up collimator 13 for expanding the beam caliber of a laser beam oscillated from the laser oscillator 10;

an amplifier 14 for amplifying the laser beam emitted from the up collimator 13;

an amplifier power source 15 for driving the amplifier 14;

a rectangular prism 16 for changing a direction of irradiation of the laser beam emitted from the amplifier 14;

a focusing lens 18 for converging the laser beam onto the surface of a sample 20;

a spectroscope optical system 24 formed of a concave mirror for example, for forming an image of the light emitted by the irradiation of laser from the surface of the sample 20 directed in a predetermined direction relative to the laser beam at an inlet slit 26 of a spectroscope 22;

the spectroscope 22 for separating the light emitted from the sample 20 whose image is formed at the inlet slit 26 into spectral lines by a diffraction grating and the like;

one or two monitoring light detectors 28 for detecting the intensity of a spectral line having a wavelength for monitoring out of the spectral lines separated by the spectroscope 22 to convert the same into an electric signal;

a measuring light detector 30 for detecting the intensity of a spectral line of an element to be measured to convert the same into an electric signal;

a spectral line intensity monitor 32 for detecting whether an intensity of a preset spectral line or an intensity ratio between a pair of preset spectral lines in the light emitted from the sample is within a preset range in accordance with an output from the light detector 28 for monitoring;

a gate circuit 34 to be opened by the spectral line intensity monitor 32 when the intensity of the preset spectral line or the intensity ratio between the pair of preset spectral lines in the light emitted from the sample is within the preset range; and an indication section 36 for obtaining a measured value from an output of the light detector 30 for measuring, when the gate circuit 34 is opened, to indicate the same.

A ruby laser having a wavelength of 0.69 micrometer or an infrared laser having a wavelength of 1.05 to 1.06 micrometer, may for example be used as the laser oscillator 10.

To maintain the density of laser below a predetermined value, the laser substance used in the amplifier 14 is larger in caliber than that of the laser oscillator 10. The up collimator 13 is used to offset the differences in caliber of these laser substances.

The rectangular prism 16 is used to cause the laser to irradiate the surface of the sample 20 at an angle of a predetermined value, and, when a laser emission section including a laser oscillator 10 is provided in a predetermined direction from the beginning, the rectangular prism 16 can be dispensed with.

Description will now be given of the operation of an embodiment of the claimed invention.

Firstly, electric energy accumulated in the power source 11 for the oscillator and a power source 15 for the amplifier is transmitted to the laser substances in the laser oscillator 10 and the amplifier 14 to excite the laser substances. When the energy of a predetermined value is accumulated in the laser substance of the laser oscillator 10, a signal is delivered to the power source 12 for the high speed switching element to actuate the same, and the energy accumulated in the laser oscillator 10 is released at once. The mode lock mechanism is assembled into the laser oscillator 10, and the released pulse-shaped laser beam is formed into the guass distribution type $TEM_{00}$ mode. The laser beam oscillated from the laser oscillator 10 falls into the amplifier 14 through the up collimator 13. Then, the energy accumulated in this amplifier 14 is also released in a moment, whereby the laser beam is further intensified. The powerful laser pulses thus obtained are converged onto the surface of the sample 20 through the rectangular prism 16 and the focusing lens 18. Then, the surface of the sample 20 is locally heated for a short period of time to thereby be formed into a plasma. At this time, the light emitted from the plasma is led to the spectroscope 22 by the spectroscope optical system 24, and dispersed by the diffraction grating and the like of the spectroscope 22. Out of dispersed lights, a spectral line having a specified wavelength for monitoring is detected by the monitoring light detector 28, and, in the spectral line intensity monitor 32, it is determined whether the intensity of the preset spectral line or the intensity ratio of the pair of preset spectral lines is within the preset range or not. Only when the intensity of the spectral line or the intensity ratio is within the preset range, the gate circuit 34 is opened, and the output of the measuring light detector 30 which has received the spectral line of the element to be measured is delivered to the indication section 36, where the result of measurement is indicated. The intensity of the spectral line of the element to be measured thus obtained is data processed by an ordinary method.

What is claimed is:

1. A method of laser emission spectroscopial analysis, wherein the light emitted from the surface of a sample when a pulsed laser beam irradiates the surface of the sample is spectroscopically analyzed, characterized in that said method includes the steps of:
   (1) fixing the emission mode of the laser beam to a guass distribution type $TEM_{00}$ mode; and
   (2) measuring the spectral line intensity of a sample element only when the intensity ratio between a pair of preset spectral lines in the light emitted from the sample is within a preset range.

2. A method of laser emission spectroscopial analysis as set forth in claim 1, wherein said pair of preset spectral lines are two Fe spectral lines of 271.4 nanometer and 273.1 nanometer wavelengths.

3. An apparatus for laser emission spectroscopial analysis, comprising:
   a laser oscillating means for oscillating a pulsed laser beam, wherein the emission mode of said laser oscillating means is fixed to a guass distribution type $TEM_{00}$;
   an amplifying means for amplifying the laser beam oscillated from said laser oscillating means;
   a focusing lens for focusing the laser beam emitted from said amplifying means onto the surface of a sample;
   a spectral separating means for spectrally separating the light emitted from the surface of said sample;
   a monitoring light detecting means for measuring the intensity of a preset spectral line in the light emitted from said sample;
   a measuring light detecting means for measuring the intensity of a spectral line of a sample element and converting the spectral line into an electric signal;
   a spectral line intensity monitor for determining whether the intensity of the preset spectral line in the light emitted from said sample is within a preset range in accordance with an output from said monitoring light detecting means;
   a gate means to be opened by said spectral line intensity monitor when the intensity of the preset spectral line in the light from said sample is within the preset range; and
   an indicating means for obtaining and indicating measurement of the output of said measuring light detecting means, when said gate means is opened.

4. An apparatus for laser emission spectroscopial analysis as set forth in claim 3, wherein said laser oscillating means is a ruby laser or an infrared laser, into which a mechanism for mode lock is assembled.

5. An apparatus for laser emission spectroscopical analysis as set forth in claim 3, wherein a laser substance used in said amplifying means is larger in caliber than that used in said laser oscillating means, and an up collimator for offsetting the difference in caliber between the laser substances used.

6. An apparatus for laser emission spectroscopical analysis, comprising:
   a laser oscillating means for oscillating a pulsed laser beam, wherein the emission mode of said laser oscillating means is fixed to a guass distribution type $TEM_{00}$;
   an amplifying means for amplifying the laser beam oscillated from said laser oscillating means;
   a focusing lens for focusing the laser beam emitted from said amplifying means onto the surface of a sample;
   a spectral separating means for spectrally separating the light emitted from the surface of said sample;
   dual monitoring light detecting means for measuring the intensities of a pair of preset spectral lines in the light emitted from said sample;
   a measuring light detecting means for measuring the intensity of a spectral line of a sample element and converting the spectral line into an electric signal;
   a spectral line intensity monitor for determining whether the intensity ratio between the preset spectral lines in the light emitted from said sample is within a preset range is accordance with the output of the monitoring light detecting means;

a gate means to be opened by said spectral line intensity monitor when the intensity ratio between the pair of preset spectral lines in the light from said sample is within the preset range; and an indicating means for measuring and indicating the output of said measuring light detecting means, when said gate means is opened.

* * * * *